United States Patent [19]

Stanek et al.

[11] Patent Number: 5,169,867
[45] Date of Patent: Dec. 8, 1992

[54] HYDROXYLAMINE COMPOUNDS

[75] Inventors: Jaroslav Stanek, Arlesheim; Jörg Frei, Hölstein, both of Switzerland

[73] Assignee: Ciba-Geigy Coporation, Ardsley, N.Y.

[21] Appl. No.: 694,220

[22] Filed: Apr. 8, 1991

[30] Foreign Application Priority Data

Apr. 11, 1990 [CH] Switzerland .................. 1248/90
May 2, 1990 [CH] Switzerland .................. 1480/90

[51] Int. Cl.⁵ .................. A61K 31/13; A61K 31/15; C07C 251/58; C07C 239/20
[52] U.S. Cl. .................. 514/645; 514/89; 514/311; 514/357; 514/538; 514/546; 514/549; 514/560; 514/640; 514/895; 560/39; 560/261; 562/564; 564/256; 564/301
[58] Field of Search .................. 564/301, 256; 514/645, 514/89, 357, 311, 538, 546, 549, 560, 640, 895; 546/25, 176, 338; 560/39, 261; 562/564

[56] References Cited

U.S. PATENT DOCUMENTS

| | | | |
|---|---|---|---|
| 3,558,690 | 1/1971 | Sallmann et al. | 260/471 |
| 3,937,841 | 2/1976 | Dijk et al. | 424/327 |
| 4,038,317 | 7/1977 | Wermuth et al. | 260/566 AE |
| 4,404,384 | 9/1983 | Gebert et al. | 544/394 |
| 4,707,498 | 11/1987 | Kolb et al. | 514/631 |
| 4,766,151 | 8/1988 | Leclerc | 514/640 |
| 4,803,286 | 2/1989 | Baldwin et al. | 514/431 |

FOREIGN PATENT DOCUMENTS

| | | |
|---|---|---|
| 184112 | 6/1986 | European Pat. Off. |
| 288055 | 10/1988 | European Pat. Off. |
| 0369944 | 9/1989 | European Pat. Off. |
| 8402908 | 8/1984 | PCT Int'l Appl. |
| 641757 | 3/1984 | Switzerland |

OTHER PUBLICATIONS

Abstract of EP 369944 (May 1990).
Biochem. Biophys. Res. Common. 130 (1985) 596-602.
J. Med. Chem. 1984, 27, 1291-1294.
Chem. Abstr. vol. 110: 20327e (1989).
Chem. Abstr. 100: 138693t (1984).
J. Med. Chem. 1980, 23, 620-624.

Primary Examiner—Richard L. Raymond
Assistant Examiner—P. O'Sullivan
Attorney, Agent, or Firm—Irving M. Fishman; Karen G. Kaiser

[57] ABSTRACT

Compounds of formula

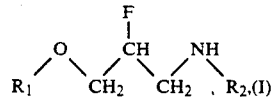

wherein $R_1$ is amino or is a radical

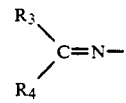

wherein $R_3$ is lower alkyl, hydroxy-lower alkyl, lower alkoxy-lower alkyl, carboxy, lower alkoxycarbonyl, phenyl, phenyl substituted by lower alkyl, halo-lower alkyl, hydroxy-lower alkyl, halogen, hydroxy, lower alkoxy, lower alkanoyloxy and/or by nitro, pyridyl, pyridyl substituted by lower alkyl, hydroxy-lower alkyl, lower alkoxy-lower alkyl, phosphonooxy-lower alkyl, lower alkanoyl, carboxy, lower alkoxycarbonyl, hydroxy, lower alkoxy, lower alkanoyloxy, nitro and-/or by oxido, or quinolyl, $R_4$ is hydrogen, lower alkyl, hydroxy-lower alkyl or halo-lower alkyl, or $R_3$ and $R_4$ together are $C_4$–$C_6$alkylene or benzo-$C_4$–$C_6$alkylene, and $R_2$ is straight-chain $C_1$–$C_4$alkyl, and salts thereof, have a strong specific inhibitory action on the enzyme ornithine decarboxylase. The compounds of Formula I are prepared according to processes known per se.

8 Claims, No Drawings

HYDROXYLAMINE COMPOUNDS

The invention relates to compounds of formula

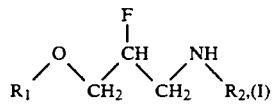

wherein $R_1$ is amino or is a radical

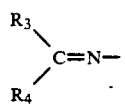

wherein $R_3$ is lower alkyl, hydroxy-lower alkyl, lower alkoxy-lower alkyl, carboxy, lower alkoxycarbonyl, phenyl, phenyl substituted by lower alkyl, halo-lower alkyl, hydroxy-lower alkyl, halogen, hydroxy, lower alkoxy, lower alkanoyloxy and/or by nitro, pyridyl, pyridyl substituted by lower alkyl, hydroxy-lower alkyl, lower alkoxy-lower alkyl, phosphonooxy-lower alkyl, lower alkanoyl, carboxy, lower alkoxycarbonyl, hydroxy, lower alkoxy, lower alkanoyloxy, nitro and/or by oxido, or quinolyl, $R_4$ is hydrogen, lower alkyl, hydroxy-lower alkyl or halo-lower alkyl, or $R_3$ and $R_4$ together are $C_4$–$C_6$alkylene or benzo-$C_4$–$C_6$alkylene, and $R_2$ is straight-chain $C_1$–$C_4$alkyl, and salts thereof, to processes for the preparation of those compounds, to pharmaceutical compositions comprising those compounds, to the use of those compounds for the therapeutic treatment of the human or animal body and for the manufacture of pharmaceutical compositions.

The general terms used hereinabove and hereinbelow have the following meanings within the scope of this Application:

The term "lower" indicates a radical having from 1 to 7, and especially from 1 to 4, carbon atoms.

Lower alkyl is, for example, n-propyl, isopropyl, n-butyl, isobutyl, sec-butyl, tert-butyl, n-pentyl, neopentyl, n-hexyl or n-heptyl, preferably ethyl and especially methyl, while straight-chain $C_1$–$C_4$alkyl is n-propyl, n-butyl and especially ethyl or methyl.

Hydroxy-lower alkyl is, for example, hydroxymethyl or 2-hydroxyethyl, and as a radical $R_3$ also polyhydroxy-lower alkyl, such as 1,2-dihydroxyethyl, 1,2,3-trihydroxypropyl, 1,2,3,4-tetrahydroxybutyl and especially 1,2,3,4,5-pentahydroxypentyl. Compounds of formula I wherein $R_1$ is a radical $R_3R_4C=N-$, $R_3$ is polyhydroxy-lower alkyl and $R_4$ is hydrogen or hydroxymethyl, are preferably derived from sugars, especially aldo- or keto-(trioses, tetroses, pentoses or hexoses). Very especially preferred is the radical $R_3R_4C=N-$ wherein $R_3$ is 1,2,3,4,5-pentahydroxypentyl (derived from D-glucose) and $R_4$ is hydrogen.

Lower alkoxy-lower alkyl is, for example, methoxymethyl or ethoxymethyl.

Lower alkoxycarbonyl is, for example, propoxycarbonyl or butoxycarbonyl, preferably methoxycarbonyl or ethoxycarbonyl.

Halogen is especially chlorine or fluorine, but may also be bromine.

Halo-lower alkyl is, for example, difluoromethyl or trifluoromethyl, also 1-chloroethyl.

Lower alkoxy is, for example, n-propoxy, isopropoxy, n-butoxy or tert-butoxy, preferably ethoxy, and especially methoxy.

Lower alkanoyloxy is, for example, formyloxy, propionyloxy or butyryloxy, and especially acetoxy.

Phosphonooxy-lower alkyl is, for example, phosphonooxymethyl [$-CH_2-O-P(=O)(OH)_2$].

Lower alkanoyl is, for example, formyl, propionyl or butyryl, and especially acetyl.

A radical $R_3R_4C=N-$ wherein $R_3$ $R_4$ together are $C_4$–$C_6$alkylene is to be understood as being cycloalkylideneamino having from 5 to 7 ring carbon atoms, for example cyclopentylideneamino or cyclohexylideneamino.

A radical $R_3R_4C=N-$ wherein $R_3$ and $R_4$ together are benzo-$C_4$–$C_6$alkylene is to be understood as being, for example, cyclopentylideneamino or cyclohexylideneamino each of which carries a fused benzo ring.

Substituted phenyl radicals $R_3$ carry especially one or two of the substituents indicated, while substituted pyridyl radicals $R_3$ carry especially from one or three of the substituents indicated. With the exception of nitro, which can be bonded only to a ring carbon atom, and oxido, which can be bonded only to a ring nitrogen atom, the indicated substituents of the pyridine radical may be bonded to ring carbon atoms or to ring nitrogen atoms. Pyridyl is, for example, 2-, 3- or 4-pyridyl, and quinolyl is, for example, 2- or 4-quinolyl.

Salts of compounds according to the invention are especially pharmaceutically acceptable, non-toxic salts. For example, compounds of formula I having basic groups may form acid addition salts, for example with inorganic acids, such as hydrochloric acid, sulfuric acid or phosphoric acid, or with suitable organic carboxylic or sulfonic acids, for example acetic acid, fumaric acid, oxalic acid or methanesulfonic acid, or, for example, with amino acids, such as glutamic acid. When several basic groups are present, mono- or poly-salts may be formed. Compounds of formula I having an acidic group, for example carboxy, and a basic group, for example amino, may be, for example, in the form of internal salts, that is to say in zwitterionic form, or part of the molecule may be in the form of an internal salt and another part may be in the form of a normal salt.

For the purposes of isolation or purification it is also possible to use pharmaceutically unacceptable salts, for example picrates or perchlorates. Only the pharmaceutically acceptable, non-toxic salts are used therapeutically and these are therefore preferred.

The compounds of the present invention may be in the form of mixtures of isomers or in the form of pure isomers, and also in the form of racemates or optically active compounds.

The compounds according to the invention have valuable, especially pharmacologically acceptable, properties. In particular, they have a strong, specific inhibitory action on the enzyme ornithine decarboxylase (ODC). ODC as a key enzyme plays an important part in the polyamine biosynthesis which takes place in virtually all cells of mammals, including humans. The polyamine concentration in the cell is regulated by ODC. Inhibition of the ODC enzyme results in a reduction in the polyamine concentration. Since a reduction in the polyamine concentration effects inhibition of cell growth, it is possible by administering ODC-inhibiting substances to inhibit the growth of both eukaryotic and prokaryotic cells, and especially of cells undergoing rapid or uncontrollable growth, and even to kill cells or to inhibit the onset of cell differentiation.

The inhibition of the ODC enzyme can be demonstrated, for example, using the method of J. E. Seely and A. E. Pegg, Ornithine decarboxylase (mouse kidney), pages 158-161, in H. Tabor and C. White Tabor (Ed.): Methods in Enzymology, Vol. 94: Polyamines, Academic Press, New York 1983.

The compounds of formula I have anti-proliferative properties which may be demonstrated directly, for example, in the following test in which the inhibitory action of the compounds of formula I on the growth of human T24 bladder carcinoma cells is determined. These cells are incubated in "Eagles's minimal essential medium", to which 5% (v/v) foetal calf serum has been added, in a humidified incubator at 37° C. and 5% by volume $CO_2$ in the air. The carcinoma cells (1000-1500) are inoculated into 96-well microtitre plates and incubated overnight under the above-mentioned conditions. The test compound is added in serial dilutions on day 1. The plates are incubated under the above-mentioned conditions for 5 days. During this period, the control cultures undergo at least four cell divisions. After incubation the cells are fixed with 3.3% (weight/volume) aqueous glutaraldehyde solution, washed with water and stained with 0.05% (w/v) aqueous methylene blue solution. After washing, the dye is eluted with 3% (w/v) aqueous hydrochloric acid. The optical density (OD) per well, which is directly proportional to the number of cells, is then measured using a photometer (Titertek multiskan) at 665 nm. The $IC_{50}$ values are calculated with a computer system using the formula $$\frac{OD_{665}(test) - OD_{655}(start)}{OD_{665}(control) - OD_{665}(start)} \times 100.$$

The $IC_{50}$ value is defined as that active ingredient concentration at which the number of cells per well at the end of the incubation period constitutes only 50% of the number of cells in the control cultures.

The compounds of formula I are therefore, for example, suitable for the treatment of benign and malignant tumours. They can bring about the regression of tumours and also prevent the spread of tumour cells and the growth of micrometastases. Furthermore, they can be used, for example, for the treatment of protozoa infections, for example trypanosomiasis, malaria, or pulmonary inflammation caused by *Pneumocystis carinii.*

The invention relates especially to compounds of formula I wherein $R_1$ is amino or is a radical

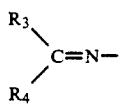

wherein $R_3$ is lower alkyl, hydroxy-lower alkyl, lower alkoxy-lower alkyl, phenyl, hydroxy-substituted phenyl, pyridyl, pyridyl substituted by hydroxy, lower alkyl, hydroxy-lower alkyl and/or by phosphonooxy-lower alkyl, or quinolyl, $R_4$ is hydrogen, lower alkyl or halo-lower alkyl, or $R_3$ and $R_4$ together are $C_4$-$C_6$alkylene or benzo-$C_4$-$C_6$-alkylene, and $R_2$ is straight-chain $C_1$-$C_4$alkyl, and salts thereof.

The invention relates more especially to compounds of formula I wherein $R_1$ is amino or is a radical

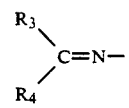

wherein $R_3$ is lower alkyl, hydroxy-substituted phenyl, or pyridyl substituted by hydroxy, lower alkyl, hydroxy-lower alkyl and/or by phosphonooxy-lower alkyl, $R_4$ is hydrogen or lower alkyl, and $R_2$ is straight-chain $C_1$-$C_4$alkyl, and salts thereof.

The invention relates preferably to compounds of formula I wherein $R_1$ is amino and $R_2$ is straight-chain $C_1$-$C_4$alkyl, and salts thereof.

The invention relates most especially to the specific compounds described in the Examples and pharmaceutically acceptable salts thereof.

The novel compounds of formula I can be prepared in a manner known per se, for example by (a) reacting a compound of formula II

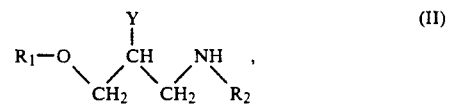

wherein $R_1$ and $R_2$ are as defined for formula I and Y is a group that can be converted into fluorine or replaced by fluorine, with a fluorinating agent, or (b) for the preparation of compounds of formula I wherein $R_1$ is amino, in a compound of formula

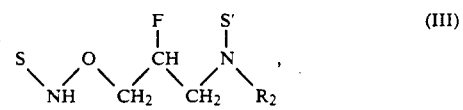

wherein $R_2$ is as defined for formula I and S and S' are each independently of the other an amino-protecting group or hydrogen, at least one of the groups S and S' being an amino-protecting group, removing the amino-protecting group(s), or (c) for the preparation of compounds of formula I wherein $R_1$ is amino, reacting a compound of formula

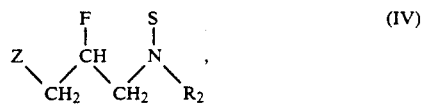

wherein $R_2$ is as defined for formula I, Z is hydroxy or a nucleofugal leaving group and S is an amino-protecting group or hydrogen, with free or N-protected hydroxylamine and, where appropriate, removing the amino-protecting group, or (d) reducing a compound of formula

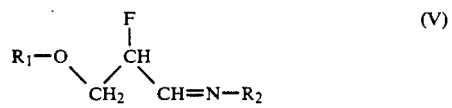

wherein $R_1$ and $R_2$ are as defined for formula I; and, if desired, converting a resulting compound of formula I into a different compound of formula I and/or, if desired, converting a resulting salt into the free compound or into a different salt and/or, if desired, converting a resulting free compound into a salt and/or separating a resulting mixture of isomeric compounds of formula I into the individual isomers.

In the following, more detailed description of processes (a) to (d), the symbols $R_1$ and $R_2$ are each as defined for formula I, unless otherwise indicated.

Process (a): A group Y that can be converted into fluorine or replaced by fluorine is, for example, hydroxy, halogen (chlorine, bromine, iodine) or aliphatically or aromatically substituted sulfonyloxy, for example methylsulfonyloxy or 4-methylphenylsulfonyloxy (tosyloxy). Y is preferably hydroxy.

Fluorinating agents that are suitable for converting hydroxy into fluorine are, for example, hydrogen fluoride, sulfur tetrafluoride, especially a mixture of hydrogen fluoride and sulfur tetrafluoride, and also, for example, substituted amino-sulfur trifluorides, such as diethylamino-sulfur trifluoride (DAST) or piperidino-sulfur trifluoride.

Compounds of formula II wherein Y is arylsulfonyloxy, for example tosyloxy, or halogen, such as chlorine, bromine or iodine, can be converted into compounds of formula I also, for example, by reaction with $KHF_2$, for example in 1,2-dihydroxyethane.

Particularly in the case of the last-mentioned reaction it may be necessary, prior to performing the reaction, to protect the amino groups in the compounds of formula II by amino-protecting groups, for example those mentioned below. After the reaction the amino-protecting groups are then removed again in a manner known per se.

The starting compounds of formula II wherein Y is hydroxy are prepared, for example, by reacting a compound of formula

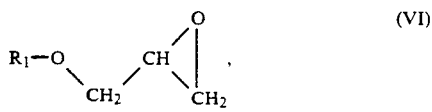

wherein $R_1$ is as defined for formula I, with an amine of the formula $R_2NH_2$ wherein $R_2$ is as defined for formula I. The starting compounds of formula II wherein Y is aliphatically or aromatically substituted sulfonyloxy are preferably prepared in a manner known per se from compounds of formula II wherein Y is hydroxy, for example by reaction with lower alkylsulfonyl or arylsulfonyl chlorides.

The reaction of the epoxide of formula VI with the amine of the formula $NH_2R_2$ is carried out without a solvent or in the presence of a solvent, for example a lower alkanol or ether, such as isopropanol or tetahydrofuran, and, where appropriate, under elevated pressure, and is effected selectively at the terminal carbon atom of the oxiranyl radical.

The starting compounds of formula VI are obtained, for example, by reacting a hydroxylamine or oxime of the formula $R_1$—OH with, for example, epichlorohydrin, epibromohydrin or 3-tosyloxy-1,2-epoxypropane. This reaction is preferably carried out in the presence of a base, for example sodium hydroxide, and without a solvent or in the presence of a solvent, for example acetone or acetonitrile.

If optically active epichlorohydrin, epibromohydrin or, especially, 3-tosyloxy-1,2-epoxypropane is used in the preparation of compounds of formula VI, then there are obtained stereoselectively the corresponding optically active compounds of formula VI. The use of the latter results in optically active compounds of formula II.

Process (b): Preferred monovalent amino-protecting groups S and S' are ester groups, for example lower alkyl esters and especially tert-butoxycarbonyl (BOC), acyl radicals, for example lower alkanoyl or halo-lower alkanoyl, such as, especially, acetyl, chloroacetyl or trifluoroacetyl, or an aliphatically or aromatically substituted sulfonyl group, for example methanesulfonyl or toluenesulfonyl (tosyl).

In compounds of formula III, S may also be a bivalent amino-protecting group. Preferred bivalent amino-protecting groups S are mono- or di-substituted methylidene groups, such as $=C(CH_3)_2$ or $=CH$-phenyl, and also 1-lower alkoxy-(for example methoxy or ethoxy-)lower alkylidene (for example ethylidene or 1-n-butylidene), for example $=C(CH_3)(OC_2H_5)$ or bisacyl radicals, for example the phthalyl radical, which together with the nitrogen atom to be protected forms a 1H-isoindole-1,3(2H)-dione (phthalimido group).

The mode of action of protecting groups, for example amino-protecting groups, and the methods by which they are introduced and removed are known per se and are described, for example, in J. F. W. McOmie, "Protective Groups in Organic Chemistry", Plenum Press, London and New York 1973, and T. W. Greene, "Protective Groups in Organic Synthesis", Wiley, New York 1984.

The removal of the amino-protecting groups can be effected, for example, by hydrolysis, especially in an acidic medium, for example with hydrogen chloride, dilute sulfuric acid, oxalic acid, organic sulfonic acids, for example toluene-4-sulfonic acid, or trifluoroacetic acid.

Compounds of formula III are known or are prepared by processes known per se.

Compounds of formula III are prepared, for example, by carrying out, for example, one of processes (a), (c) or (d) with the amino group(s) protected. It is also possible to prepare compounds of formula III from compounds of formula I, for example for purification purposes.

Process (c): In compounds of formula IV the nucleofugal leaving group Z is, for example, halogen, for example chlorine, bromine or iodine, and also, for example, aliphatically or aromatically substituted sulfonyloxy, for example methylsulfonyloxy or 4-methylphenylsulfonyloxy. The amino-protecting groups S in a compound of formula IV correspond to the amino-protecting groups S and S' in compounds of formula III defined under process (b).

If, in a compound of formula IV, Z is hydroxy, it is possible to carry out, for example, an intermolecular dehydration reaction. Especially suitable for this purpose is a variant of the Mitsunobu reaction [Synthesis (1976), 682] in which the compound of formula IV is reacted with an N-protected hydroxylamine derivative, for example N-hydroxyphthalimide, N-hydroxy-5-norbornene-2,3-dicarboxylic acid imide or acetohydroxamic acid ethyl ester, and, for example, triphenylphosphine and N,N'-azodicarboxylic acid diethyl ester.

If, in a compound of formula IV, Z is a nucleofugal leaving group, then process (c) corresponds to a simple nucleophilic substitution reaction (O alkylation).

Process (d): The reduction can be effected, for example, with complex metal hydrides, for example $LiBH_4$, $NaCNBH_3$, or with hydrogen in the presence of a catalyst, for example palladium on carbon.

The starting compounds of formula V can be prepared, for example, from the analogous aldehydes (=O instead of =NR$_2$ in formula V) by reaction with lower alkylamines.

The said aldehydes analogous to formula V can be prepared, for example, by oxidation, for example with pyridinium chlorochromate [see J. Org. Chem. 46, 4797 (1981)], from corresponding hydroxymethyl compounds. Furthermore, they can also be obtained by reduction of corresponding lower alkyl esters, for example with diisobutylaluminium hydride [see Chem. Pharm. Bull. 23, 3081 (1975)], or by reduction of corresponding acid chlorides, for example with tri-n-butyltin hydride [see J. Org. Chem. 25, 284 (1961) or J. Amer. Chem. Soc. 88, 571 (1966)].

The said aldehydes analogous to formula V can be obtained especially also by means of the following reaction sequence:

(1) Reaction of 3,4-0,0-isopropylidene-3,4-dihydroxy-1,2-epoxybutane [see J. Org. Chem. 52, 2841 (1987) or DE-A-3 150 917] with acetohydroxamic acid ethyl ester to form 3,4-0,0-isopropylidene-2,3,4-trihydroxy-1-(1-ethoxyethylideneaminoxy)-butane. The 2-hydroxy group in the latter can be converted into fluorine in a manner known per se.

(2) Removal of the isopropylidene group, for example by treatment with dilute acid.

(3) Glycol cleavage of the terminal α,β-dihydroxyethyl group to form formyl by reaction with NaIO$_4$ or Pb(OCOCH$_3$)$_4$.

Compounds of formula I can be converted into other compounds of formula I.

Compounds of formula I wherein R$_1$ is amino can be converted by reaction with a carbonyl compound R$_3$R$_4$C=O, wherein the carbonyl group may also be in masked form, for example in acetal or ketal form, into other compounds of formula I wherein R$_1$ is a radical

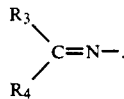

Conversely, it is also possible, for example by acid hydrolysis, to convert compounds of formula I wherein R$_1$ is a radical

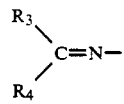

into compounds of formula I wherein R$_1$ is amino.

Free compounds of formula I obtainable in accordance with the process having salt-forming properties can be converted into their salts in a manner known per se; compounds having basic properties can be converted into their salts by treatment with acids or suitable derivatives thereof.

The compounds, including their salts, can also be obtained in the form of their hydrates, or their crystals may include, for example, the solvent used for crystallisation.

Mixtures of isomers obtainable in accordance with the invention can be separated into the individual isomers in a manner known per se; racemates can be separated, for example, by the formation of salts with optically pure salt-forming reagents and separation of the diastereoisomeric mixture so obtainable, for example by fractional crystallisation.

The above-mentioned reactions can be carried out under reaction conditions known per se, in the absence of or, usually, in the presence of solvents or diluents, preferably those solvents or diluents which are inert towards the reagents used and are solvents therefor, in the absence or presence of catalysts, condensation agents or neutralising agents, and, depending upon the nature of the reaction and/or the reactants, at reduced, normal or elevated temperature, for example in a temperature range of from approximately −80° C. to approximately 190° C., preferably from approximately −20° C. to approximately 150° C., for example at the boiling point of the solvent used, under atmospheric pressure or in a closed vessel, where appropriate under pressure, and/or in an inert atmosphere, for example under a nitrogen atmosphere.

In the processes of the present invention it is preferable to use those starting materials which result in the compounds described at the beginning as being especially valuable.

The invention relates also to those forms of the process in which a compound obtainable as intermediate at any stage of the process is used as starting material and the remaining process steps are carried out, or in which a starting material is formed under the reaction conditions or is used in the form of a derivative, for example a salt, thereof.

The present invention relates also to pharmaceutical compositions that comprise one of the pharmacologically active compounds of formula I as active ingredient. Compositions for enteral, especially oral, and for parenteral administration are especially preferred. The compositions comprise the active ingredient on its own or, preferably, together with a pharmaceutically acceptable carrier. The dosage of the active ingredient depends upon the disease to be treated and upon the species, its age, weight and individual condition, and also upon the mode of administration.

The pharmaceutical compositions comprise from approximately 5% to approximately 95% active ingredient, dosage forms in single dose form preferably comprising from approximately 20% to approximately 90% active ingredient and dosage forms that are not in single dose form preferably comprising from approximately 5% to approximately 20% active ingredient. Unit dose forms, such as dragées, tablets or capsules, comprise from approximately 0.05 g to approximately 1.0 g of active ingredient.

The pharmaceutical compositions of this invention are prepared in a manner known per se, for example by means of conventional mixing, granulating, confectioning, dissolving or lyophilising processes. For example, pharmaceutical compositions for oral use can be obtained by combining the active ingredient with one or more solid carriers, optionally granulating a resulting mixture, and, if desired, processing the mixture or granules, if necessary with the addition of additional excipients, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starches, for example corn, wheat, rice or potato starch, methylcellulose, hydroxypropylmethylcellulose, sodium carboxymethylcellulose and/or polyvinylpyrrolidone, and/or, if desired, disintegrators, such as the above-mentioned starches, also carboxymethyl starch, cross-linked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Dragée cores can be provided with suitable, optionally enteric, coatings, there being used inter alia concentrated sugar solutions which may contain gum arabic, talc, polyvinylpyrrolidone, polyethylene glycol and/or titanium dioxide, or coating solutions in suitable organic solvents or solvent mixtures, or, for the production of enteric coatings, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Orally administrable pharmaceutical compositions also include dry-filled capsules consisting of gelatin, and also soft, sealed capsules consisting of gelatin and a plasticiser, such as glycerol or sorbitol. The dry-filled capsules may contain the active ingredient in the form of granules, for example in admixture with fillers, such as corn starch, binders and/or glidants, such as talc or magnesium stearate, and optionally stabilisers. In soft capsules, the active ingredient is preferably dissolved or suspended in suitable liquid excipients, such as fatty oils, paraffin oil or liquid polyethylene glycols, to which stabilisers may also be added.

Other oral dosage forms are, for example, syrups prepared in customary manner which comprise the active ingredient, for example, in suspended form and in a concentration of about 5% to 20%, preferably about 10%, or in a similar concentration that provides a suitable single dose, for example, when administered in measures of 5 or 10 ml. Also suitable are, for example, powdered or liquid concentrates for the preparation of shakes, for example in milk. Such concentrates may also be packaged in single dose quantities.

Suitable rectally administrable pharmaceutical compositions are, for example, suppositories that consist of a combination of the active ingredient and a suppository base. Suitable suppository bases are, for example, natural or synthetic triglycerides, paraffin hydrocarbons, polyethylene glycols or higher alkanols.

For parenteral administration there are especially suitable aqueous solutions of an active ingredient in water-soluble form, for example in the form of a water-soluble salt, or aqueous injection suspensions that contain viscosity-increasing substances, for example sodium carboxymethylcellulose, sorbitol and/or dextran, and, if desired, stabilisers. The active ingredient, optionally together with excipients, can also be in the form of a lyophilisate and can be made into a solution prior to parenteral administration by the addition of suitable solvents.

Solutions such as are used, for example, for parenteral administration can also be used as infusion solutions.

The invention relates also to a method of treating the above-mentioned pathological conditions. The compounds of this invention can be administered prophylactically or therapeutically, preferably in the form of pharmaceutical compositions. In the case of an individual having a body weight of about 70 kg the daily dose administered is from approximately 0.3 g to approximately 15 g, preferably from approximately 0.5 g to approximately 5 g, of a compound of the present invention.

The following Examples illustrate the present invention; temperatures are given in degrees Celsius. The following abbreviations are used: BOC $\triangleq$ tert-butoxycarbonyl; hexane $\triangleq$ n-hexane; ether $\triangleq$ diethyl ether; THF $\triangleq$ tetrahydrofuran.

EXAMPLE 1

N-(3-aminoxy-2-fluoropropyl)-methylamine dihydrochloride 3.3 g of N,N'-di-BOC-N-(3-aminoxy-2-fluoropropyl)-methylamine are dissolved in 5 ml of ethanol; 35 ml of 2N alcoholic hydrochloric acid are added and the mixture is left to stand at room temperature for 16 hours. 100 ml of dry ether are then added. The precipitated title compound is filtered with suction, washed with ether and dried, m.p. 160° (with decomp.).

$^1$H-NMR (D$_2$O): δ5.3 and 5.15 (2 m, 1H); 4.38 (m,2H); 3.45 (m, 2H); 2.8 (s, 3H).

The starting compound is prepared as follows:

A solution of 8.0 g (50 mmol) of O-(2,3-epoxypropyl)-acetohydroxamic acid ethyl ester and 50 ml of a 33% ethanolic methylamine solution in 100 ml of isopropanol is stirred for 4 hours at 85° and then concentrated to dryness by evaporation. The resulting residue is chromatographed with ethyl acetate over 250 g of silica gel. The fractions having an Rf value of 0.21 (silica gel/methylene chloride:methanol:conc.ammonia 150:50:1) are combined and concentrated by evaporation. The yellow oil that remains behind is O-(3-methylamino-2-hydroxypropyl)-acetohydroxamic acid ethyl ester.

A mixture of 6.5 g (34 mmol) of O-(3-methylamino-2-hydroxypropyl)-acetohydroxamic acid ethyl ester in 150 ml of 2N hydrochloric acid is boiled at reflux for 4 hours and then concentrated to dryness by evaporation. The wax-like residue of N-(3-aminoxy-2-hydroxypropyl)-methylamine dihydrochloride is taken up in a small amount of water, converted into the free base by filtration over 150 ml of Dowex 1×4 ion exchanger resin (in basic form) and crystallised in the form of an oxalate salt, m.p. 130°-133° (from methanol), Rf value 0.43 (silica gel/methylene chloride:methanol:conc.ammonia 40:10:1).

4.8 g (25 mmol) of N-(3-aminoxy-2-hydroxypropyl)-methylamine dihydrochloride are dissolved at −78° in 80 g of liquid hydrogen fluoride in a Teflon autoclave. 5.6 g of sulfur tetrafluoride are introduced and the vessel is closed and left to stand for 24 hours at room temperature. After degassing, the residue is dissolved in 2N hydrochloric acid. This solution is filtered and the filtrate is neutralised, in portions, with solid sodium hydrogen carbonate; a solution of 13 g of di-tert-butyl dicarbonate in 50 ml of tetrahydrofuran is added and the mixture is left to stand for 1 hour. The reaction mixture is diluted with 200 ml of ether and the organic phase is separated off, washed with water, dried over magnesium sulfate, filtered and concentrated by evaporation. The oil that remains behind is chromatographed with a mixture of hexane:ethyl acetate 3:1 over 500 g of silica gel, yielding the starting compound in the form of a yellow oil, Rf value 0.18.

EXAMPLE 2

N-[3-(2-hydroxy-benzylideneaminoxy)-2-fluoropropyl]-methylamine hydrochloride 2.5 ml of 1N sodium hydroxide solution and 305 mg (2.5 mmol) of salicylaldehyde are added to a solution of 488 mg (2.5 mmol) of N-(3-aminoxy-2-fluoropropyl)-methylamine dihydrochloride in 10 ml of ethanol and the mixture is stirred for 24 hours at room temperature. The reaction mixture is then concentrated to dryness by evaporation and the residue is crystallised from ethanol/ether.

$^1$H-NMR (D$_2$O): δ8.45 (s, 1H); 7.4 (m, 2H); 7.0 (m, 2H); 5.28 and 5.07 (2 m, 1H); 4.46(m, 2H); 3.41 (m, 2H); 2.82 (s, 3H).

EXAMPLE 3

N-[3-(3-hydroxy-5-hydroxymethyl-2-methyl-4-pyridyl-methyleneaminoxy)-2-fluoropropyl]-methylamine hydrochloride 4.0 ml of 1N sodium hydroxide solution and 408 mg (2 mmol) of pyridoxal hydrochloride are added to a solution of 390 mg (2.0 mmol) of N-(3-aminoxy-2-fluoropropyl)-methylamine dihydrochloride in 10 ml of ethanol and the mixture is stirred for 16 hours at room temperature. The reaction mixture is then concentrated to dryness by evaporation and the title compound is crystallised from ethyl acetate.

$^1$H-NMR (D$_2$O): δ8.8(s, 1H); 8.2(s, 1H); 5.33 and 5.12 (2m, 1H); 4.86 (s, 2H); 4.65 (m, 2H); 3.42 (m, 2H); 2.78 (s, 3H); 2.66 (s, 3H).

EXAMPLE 4

N-(3-isopropylideneaminoxy-2-fluoropropyl)-methylamine hydrochloride 2.5 ml of 1N sodium hydroxide solution and 0.36 ml (5 mmol) of acetone are added to a solution of 488 mg (2.5 mmol) of N-(3-aminoxy-2-fluropropyl)-methylamine dihydrochloride in 10 ml of ethanol and the mixture is stirred for 24 hours at room temperature. The reaction mixture is then concentrated to dryness by evaporation. The residue is taken up in ethanol, filtered and crystallised by the addition of ether.

$^1$H-NMR (D$_2$O): 5.3 and 5.11 (2 m, 1H); 4.44 (m, 2H); 3.39 (m, 2H); 2.01 (s, 6H).

EXAMPLE 5

N-(3-aminoxy-2-fluoropropyl)-methylamine dihydrochloride 1.45 g (3.8 mmol) of N-(3-BOC-aminoxy-2-fluoropropyl)-N-methyl-4-toluenesulfonamide are suspended in 10 ml of water and 20 ml of conc. hydrochloric acid and heated at reflux for 6 hours. After cooling, the reaction mixture is filtered and extracted with ethyl acetate. The aqueous phase is then concentrated to dryness by evaporation and the title compound is crystallised from ethanol/ether, m.p. 160° C. (with decomp.).

$^1$H-NMR (D$_2$O); δ5.3 and 5.15 (2 m, 1H); 4.38 (m, 2H); 3.45 (m, 2H); 2.8 (s, 3H).

The starting compounds are prepared as follows:

(a) 3-Aminoxy-2-fluoropropylamine dihydrochloride

In a 200 ml Teflon reactor, 2.5 g of 3-aminoxy-2-hydroxypropylamine (see DE 2 651 083) are dissolved at −78° in 40 g of liquid hydrogen fluoride (HF). 5.6 g of sulfur tetrafluoride are then introduced. The mixture is stirred in the closed reactor for 3 hours at −78° using a magnetic rod, then heated to 0° and, after a further 24 hours, degassed, yielding crude 3-aminoxy-2-fluoropropylamine in the form of the hydrofluoride, which is converted into the corresponding pure dihydrochloride as follows:

The residue is taken up in 50 ml of 2N HCl, filtered and applied to a 35×270 mm column containing weakly basic ion exchanger MWA-1 (Dow Chemicals). The column is washed with water. The ninhydrin-positive fractions are combined, neutralised with 1N HCl and concentrated by evaporation. The residue is crystallised from ethyl acetate, yielding 3-aminoxy-2-fluoropropylamine dihydrochloride having a melting point of 204°–207°.

(b) 3-BOC-aminoxy-2-fluoropropylamine

A solution of 480 mg (2.2 mmol) of di-tert-butyl dicarbonate in 10 ml of THF is added to a solution of 362 mg (2 mmol) of 3-aminoxy-2-fluoropropylamine dihydrochloride in 25 ml of THF, 5 ml of water and 2 ml of 1N NaOH and the mixture is stirred vigorously for 16 hours at room temperature. The reaction mixture is diluted with 50 ml of ether and a further 2 ml of 1N NaOH. The organic phase is separated off, washed with water, dried over sodium sulfate and concentrated by evaporation, yielding starting compound a in the form of a yellow oil.

(c) N-(3-BOC-aminoxy-2-fluoropropyl)-4-toluenesulfonamide

While cooling with ice, a solution of 0.48 g (2.5 mmol) of toluene-4-sulfonyl chloride is added dropwise, with stirring, to a solution of 0.52 g (2.5 mmol) of 3-BOC-aminoxy-2-fluoropropylamine and 0.42 ml (3 mmol) of triethylamine in 10 ml of methylene chloride and the mixture is stirred for 16 hours at room temperature. The reaction mixture is then washed with 25 ml of 0.2N hydrochloric acid and with water, dried over magnesium sulfate, filtered and concentrated by evaporation. The residue is starting compound b.

(d) N-(3-BOC-aminoxy-2-fluoropropyl)-N-methyl-4-toluenesulfonamide 0.54 g (1.5 mmol) of N-(3-BOC-aminoxy-2-fluoropropyl)-4-toluenesulfonamide are dissolved in 10 ml of ethanol and 1.5 ml of 1N sodium hydroxide solution and, after the addition of 0.21 g (1.5 mmol) of methyl iodide, maintained at 70° for 10 hours in a bomb tube. After cooling, the reaction mixture is concentrated by evaporation and the residue is taken up in ethyl acetate. The resulting solution is washed with water and dried over magnesium sulfate, yielding, after evaporation of the solvent, starting compound c.

EXAMPLE 6

N-(3-aminoxy-2-fluoropropyl)-ethylamine dihydrochloride

Analogously to Example 5, the title compound is prepared starting from N-(3-BOC-aminoxy-2-fluoropropyl)-4-toluenesulfonamide and ethyl bromide.

$^1$H-NMR (D$_2$O): δ5.31 and 5.15 (2 m, 2H); 4.39 (m, 2H); 3.48 (m, 2H); 3.30 (m, 2H); 1.25 (t, 3H).

EXAMPLE 7

N-(3-aminoxy-2-fluoropropyl)-propylamine dihydrochloride

Analogously to Example 5, the title compound is prepared starting from N-(3-BOC-aminoxy-2-fluoropropyl)-4-toluenesulfonamide and n-propyl iodide.

$^1$H-NMR (D$_2$O): δ5.29 and 5.06 (2m, 1H); 4.43 (m, 2H); 3.21–3.5 (m, 6H); 1.21 (t, 3H).

EXAMPLE 8

N-(3-aminoxy-2-fluoropropyl)-n-butylamine dihydrochloride

Analogously to Example 5, the title compound is prepared starting from N-(3-BOC-aminoxy-2-fluoropropyl)-4-toluenesulfonamide and n-butyl iodide. $^1$H-NMR (D$_2$O): δ5.35 and 5.14 (2m, 1H); 4.46 (m, 2H); 3.25–3.43 (m, 4H); 2.3–2.8 (m,4H); 1.2 (t, 3H).

EXAMPLE 9

N-(3-aminoxy-2fluoropropyl)-ethylamine dihydrochloride

A mixture of 1.0 g (3 mmol) of N-ethyl-N-[3-(1-methylethylideneaminooxy)-2-fluoropropyl]-4-toluenesulfonamide in 10 ml of water and 20 ml of conc. hydrochloric acid is heated at reflux for 10 hours and then concentrated to half its volume under normal pressure. After cooling, the reaction mixture is filtered, washed with ether and concentrated to dryness by evaporation. The residue is the tittle compound.

$^1$H-NMR (D$_2$O): δ1.25 (t, 3H); 3.30 (m, 2H); 3.48 (m, 2H); 4.39 (m, 2H); 5.15 and 5.31 (2m, 1H).

The starting compounds are prepared as follows:

a: N-[3-(1-methyl-ethylideneaminooxy)-2-fluoropropyl]-4-toluenesulfonamide A solution of 0.52 g (2.8 mmol) of toluene-4-sulfonyl chloride in 10 ml of THF, and 8.1 ml of 1N NaOH are added in succession, with stirring, to a solution of 0.5 g (2.7 mmol) of 3-(1-methyl-ethylideneaminooxy)-2-fluoropropylamine hydrochloride in 10 ml of water. The reaction mixture is stirred for 6 hours at room temperature and diluted with 100 ml of ethyl acetate. The organic phase is separated off, washed with 50 ml of 0.5N HCl and water, dried over magnesium sulfate and concentrated by evaporation. The oily yellow residue is starting compound a.

$^1$H-NMR (CDCl$_3$): δ1.82 (s, 6H); 2.43 (s, 3H); 3.1–3.4 (m, 2H); 4.0–4.42 (m, 2H); 4.6 and 4.85 (2m, 1H); 4.96 (t, 1H); 7.31 (d, 2H); 7.74 (d, 2H).

b: N-ethyl-N-[3-(1-methyl-ethylideneaminooxy)-2-fluoropropyl]-4-toluenesulfonamide 0.415 g (3 mmol) of potassium carbonate and 0.13 ml (1.8 mmol) of ethyl bromide are added to a solution of 0.36 g (1.2 mmol) of N-[3-(1-methyl-ethylideneaminooxy)-2-fluoropropyl]-4-toluenesulfonamide in 2 ml of DMF and the mixture is stirred for 24 hours at room temperature. The reaction mixture is then diluted with 20 ml of ethyl acetate and filtered. The filtrate is washed with water, dried over magnesium sulfate, filtered and concentrated by evaporation. The resulting residue is starting compound b.

$^1$H-NMR (CDCl$_3$): δ1.12 (t, 3H); 1.83 (3, 6H); 2.40 (s, 3H); 3.10–3.66 (m, 4H); 4.18 (q, 2H); 4.76 and 5.01 (2m, 1H); 7.27 (d, 2H); 7.66 (d, 2H).

EXAMPLE 10

N-(3-aminoxy-2-fluoropropyl)-propylamine dihydrochloride

Analogously to Example 9, the title compound is prepared starting from N-[3-(1-methylethylideneaminooxy)-2-fluoropropyl]-4-toluenesulfonamide and n-propyl iodide.

$^1$H-NMR (D$_2$O): δ5.29 and 5.06 (2m, 1H); 4.43 (m, 2H); 3.21–3.5 (m, 6H); 1.21 (t, 3H).

EXAMPLE 11

N-(3-aminoxy-2-fluoropropyl)-n-butylamine dihydrochloride

Analogously to Example 9, the title compound is prepared starting from N-[3-(1-methylethylideneaminoxy)-2-fluoropropyl]-4-toluenesulfonamide and n-butyl iodide.

hu 1H-NMR (D$_2$O): δ5.35 and 5.14 (2m, 1H); 4.46 (m, 2H); 3.25–3.43 (m, 4H); 2.3–2.8 (m, 4H); 1.2 (t, 3H).

EXAMPLE 12

Capsules comprising 0.25 g of active ingredient, for example one of the compounds of Examples 1 and 2, can be prepared as follows:

| Composition(for 5000 capsules) | |
|---|---|
| active ingredient | 1250 g |
| talc | 180 g |
| wheat starch | 120 g |
| magnesium stearate | 80 g |
| lactose | 20 g |

The pulverulent substances are forced through a sieve of 0.6 mm mesh size and mixed together. 0.33 g portions of the mixture are introduced into gelatin capsules using a capsule-filling machine.

What is claimed is:

1. A compound of formula

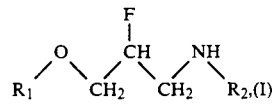

wherein R$_1$ is amino or is a radical

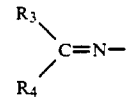

wherein R$_3$ is lower alkyl, hydroxy-lower alkyl, lower alkoxy-lower alkyl, carboxy, lower alkoxycarbonyl, phenyl, phenyl substituted by lower alkyl, halo-lower alkyl, hydroxy-lower alkyl, halogen, hydroxy, lower alkoxy, lower alkanoloxy and/or by nitro, pyridyl, pyridyl substituted by lower alkyl, hydroxy-lower alkyl, lower alkoxy-lower alkyl, phosphonooxy-lower alkyl, lower alkanoyl, carboxy, lower alkoxycarbonyl, hydroxy, lower alkoxy, lower alkanoyloxy, nitro and/or by oxido, or quinolyl, R$_4$ is hydrogen, lower alkyl, hydroxy-lower alkyl or halo-lower alkyl, or R$_3$ and R$_4$ together are C$_4$–C$_6$ alkylene or benzo-C$_4$–C$_6$alkylene, and R$_2$ is straight-chain C$_1$–C$_4$ alkyl, or a salt thereof.

2. A compound of formula I according to claim 1, wherein R$_1$ is amino or is a radical

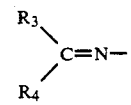

wherein R$_3$ is lower alkyl, hydroxy-lower alkyl, lower alkoxy-lower alkyl, phenyl, hydroxy-substituted phenyl, pyridyl, pyridyl substituted by hydroxy, lower alkyl, hydroxy-lower alkyl and/or by phosphonooxy-lower alkyl, or quinolyl, R₄ is hydrogen, lower alkyl or halo-lower alkyl, or R₃ and R₄ together are C₄-C₆alkylene or benzo-C₄-C₆-alkylene, and R₂ is straight-chain C₁-C₄alkyl, or a salt thereof.

3. A compound of formula I according to claim 1, wherein R₁ is amino or is a radical

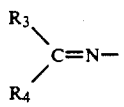

wherein R₃ is lower alkyl, hydroxy-substituted phenyl, or pyridyl substituted by hydroxy, lower alkyl, hydroxy-lower alkyl and/or by phosphonooxy-lower alkyl, R₄ is hydrogen or lower alkyl, and R₂ is straight-chain C₁-C₄alkyl, or a salt thereof.

4. A compound of formula I according to claim 1, wherein R₁ is amino and R₂ is straight-chain C₁-C₄ alkyl, or a salt thereof.

5. A pharmaceutically acceptable salt of a compound of formula I according to claim 1.

6. N-(3-aminoxy-2-fluoropropyl)-methylamine or a pharmaceutically acceptable salt thereof according to claim 1.

7. A pharmaceutical composition for the treatment of diseases responsive to ornithine decarboxylase inhibition comprisng an ornithine decarboxylase inhibiting effective amount of a compound of formula I according to claim 1 and a pharmaceutically acceptable carrier.

8. A method of treating diseases that respond to inhibition of ornithine decarboxylase comprising administering to said mammal a therapeutically effective amount of a compound of the formula I according to claim 1.

* * * * *

UNITED STATES PATENT AND TRADEMARK OFFICE
CERTIFICATE OF CORRECTION

PATENT NO. : 5,169,867
DATED : December 8, 1992
INVENTOR(S) : Jaroslav Stanek & Jorg Frei It is certified that error appears in the above-identified patent and that said Letters Patent is hereby corrected as shown below:

Column 14, line 49 replace -- alkanoloxy-- with "alkanoyloxy".

Signed and Sealed this

Twenty-sixth Day of October, 1993

Attest:

BRUCE LEHMAN

Attesting Officer

Commissioner of Patents and Trademarks